United States Patent [19]

Hirschfeld et al.

[11] Patent Number: 4,558,014
[45] Date of Patent: Dec. 10, 1985

[54] ASSAY APPARATUS AND METHODS

[75] Inventors: Tomas B. Hirschfeld, Livermore, Calif.; Myron J. Block, 334 N. Main St., North Salem, N.H. 03073

[73] Assignee: Myron J. Block, North Salem, N.H.

[21] Appl. No.: 503,500

[22] Filed: Jun. 13, 1983

[51] Int. Cl.⁴ .................... G01N 33/54; G01N 21/00; G01N 21/64; G01N 33/58
[52] U.S. Cl. .................................. 436/527; 422/55; 422/56; 422/57; 422/58; 422/59; 422/61; 436/535; 436/800; 436/807; 436/808; 250/227; 250/365; 356/445
[58] Field of Search .............. 436/527, 805, 535, 800, 436/807, 808; 422/55–59, 61; 356/445; 250/227, 365

[56] References Cited

U.S. PATENT DOCUMENTS

| | | | |
|---|---|---|---|
| 3,939,350 | 2/1976 | Kronick et al. | 436/805 |
| 3,998,591 | 12/1976 | Eckfeldt | 422/86 |
| 4,050,895 | 9/1977 | Hardy et al. | 436/805 |
| 4,106,909 | 8/1978 | David et al. | 436/100 |
| 4,133,639 | 1/1979 | Harte | 436/805 |
| 4,321,057 | 3/1982 | Buckles | 422/58 |
| 4,368,047 | 1/1983 | Andrade et al. | 436/805 |
| 4,399,099 | 8/1983 | Buckles | 436/527 |
| 4,447,546 | 8/1984 | Hirschfeld | 436/805 |

Primary Examiner—Christine M. Nucker
Attorney, Agent, or Firm—Schiller & Pandiscio

[57] ABSTRACT

An assay apparatus and methods employing total internal fluorescence to define a thin observed volume of a multi-phase suspension from which the suspended phase, because of its size and shape, is substantially excluded. Observations of the fluorescence of a known quantity of fluorescent material introduced into a known volume of the sample containing the observed volume permits quantitation of the volumes of the suspended and suspending phases.

10 Claims, 4 Drawing Figures

ASSAY APPARATUS AND METHODS

BACKGROUND OF THE INVENTION

This invention relates to chemical and biochemical assays, and more particularly to such assays wherein the volume, relative to a given sample volume, of at least one of the constituent phases of a fluid suspension is to be quantitated without physically separating the phases from one another.

A problem frequently encountered in the assay of fluid suspensions is to determine the volume, relative to the total volume, of one or more of the constituent phases. Thus, for instance, in the assay of milk, it is frequently desired to determine the percentage butterfat content. As another example, in the assay of whole blood, the percentage cellular volume [generally expressed as a packed cell volume (PCV) or hematocrit] is frequently desired. Such relative volumes are commonly determined after the constituent phases of the suspension are physically separated from one another, as by centrifugation.

Not only is such a separation step a typical preliminary to the quantitation of the constituent phases of a suspension, it is also generally a preliminary to yet other assays. Thus, to consider again the assay of blood, a large number of protocols require a serum sample, the blood first being centrifuged to separate from the serum the approximately 50% volume of cells. As a consequence, any protocol permitting the use of whole blood requires a correction for cell volume to relate the whole blood measures to the serum measures that constitute the accepted body of clinical data. Similar considerations occur with respect to the assay of a constituent phase of other suspensions.

A particular class of assays that may incorporate the present invention are immunoassays. Such assays, in which aliquots of sample and one or more reagents are variously reacted to form antigen-antibody or similar complexes which may then be observed in order to assay the sample for the presence and titer of a predetermined moiety of the complex, are well known. Typical of such assays are those wherein a specific antibody is used to measure the quantity of the antigen for which it is specific (or vice versa). However, the technique has been extended to quantitate haptens (including hormones, alkaloids, steroids, and the like) as well as antigens, and antibody fragments (i.e., Fab) as well as complete antibodies, and it is in this broader sense that the present invention should be understood.

As is well known, sensitive immunoassays employ tracer techniques wherein a tagged constituent of the complex is incorporated into the reagent, the non-complexed tagged reagent being separated from the complexed reagent, and the complex (or non-complexed reagent) then quantitated by observing the tag. Both radioisotopes and fluorescent markers have been used to tag constituents of immunoassay reagents, the tag being respectively observed by a gamma ray counter or a fluorimeter. The present invention is, however, directed only to those assays which rely on fluorescence.

The separation of the non-complexed tagged moiety from the complexed is commonly accomplished by immobilizing a predetermined one of the components of the complex to a solid phase (such as the inside wall of a test tube, glass or polymeric beads, or the like) so as hopefully not to hinder the component's reactivity in forming the complex. As an example, an antibody such as immunoglobulin G (IgG) may be bound to a solid phase, such as glass, by a silyl compound such as 3-aminopropyltrimethoxy silane, through the use of bifunctional reagents such as phenyl diisothiocyanate. Any complex formed incorporating the immobilized component may then be physically separated from the non-reacted complement remaining in solution, as by aspirating or decanting the fluid from a tube or by eluting the fluid through a particulate bed. Alternatively, as disclosed, for instance, in copending U.S. patent application Ser. Nos. 406,324 (filed Aug. 9, 1982) and 410,340 (filed Aug. 23, 1982), total reflection fluorescence (TRF) and fluorescence tunnelling may be used to restrict the excitation and observation of fluorescence to an extremely thin layer adjacent the solid phase, thereby in effect accomplishing the separation of the immobilized tagged component from that remaining in solution by optical means.

The methods so far described are applicable to a number of immunological procedures. In competition immunoassay, for instance, the reagent consists of a known quantity of tagged complement (such as antigen) to the immobilized component of the complex (in this instance, antibody). The reagent is mixed with a fixed quantity of the sample containing the untagged complement to be quantitated. Both tagged and untagged complement attach to the immobilized component of the complex in proportion to their relative concentrations. After incubation for a set time, the fluid sample and reagent are separated. The complex immobilized to the solid phase is then illuminated with radiation of a wavelength chosen to excite fluorescence of the tag, and the fluoresence is measured. The intensity of the fluoresence of the immobilized complex is inversely proportional to the concentration of the untagged complement being assayed.

Alternatively, an assay may be made by immobilizing a quantity of an analog of the moiety to be quantitated (i.e., a substance which is immunologically similarly reactive) and reacting the sample with a known quantity of tagged complement. The tagged complement complexes with both the unknown quantity of the moiety in the sample and the immobilized analog. Again, the intensity of fluorescence of the immobilized complex is inversely proportional to the concentration of the (free) moiety being quantitated.

So-called "sandwich" immunoassays may be performed for multivalent complements to the immobilized component, the attached complement being then further reacted with a tagged analog of the immobilized component. Thus, bivalent antigen may be bound to an immobilized antibody and then reacted with a fluorescent tagged antibody, forming an antibody-antigen—tagged antibody sandwich that may then be separated from the unreacted tagged antibody. The intensity of the fluorescence of the thus formed immobilized complex is directly proportional to the concentration of the species being quantitated.

A number of problems arise in the fluorescent assay of biological fluids. Thus, for instance, erythrocytes are highly absorbing. Accordingly, prior art fluorescent assays of blood typically centrifuge the sample and assay the supernatant serum. Typical centrifugation procedures require on the order of 15 to 30 minutes, a time period that may be inconsistent with some clinical procedures where assay results are required rapidly (so-called "stat" procedures). For such cases, state-ofthe-art microsampling techniques and centrifuges do permit serum extraction in less than a minute; however, such centrifuges are not, as yet, available in all clinical laboratories, and in any event, serum extraction, by whatever means, is an additional step, and consequently a potential source for the introduction of human error. Further, means for serum extraction are not available in all settings where a rapid assay may be desireable (e.g., mobile emergency facilities, home care, and the like).

The total reflection fluorescence assay methods, as described in the aforementioned Ser. Nos. 406,324 and 410,340, by sampling an extremely thin layer of the sample, permit assays of optically dense samples. While in principle this would allow fluorescent assay of whole blood, clinical experience has generally been with serum samples, and consequently, to relate whole blood assays to the accepted body of experimental data requires a quantitation of the serum volume of the sample. A similar consideration occurs with other biological fluids, such as saliva, wherein the sample as collected is also typically a disperse system with an unknown ratio of suspended-to-suspending material (e.g., for saliva, an unknown ratio of bubble to fluid volumes).

OBJECTS OF THE INVENTION

Accordingly, it is an object of the present invention to provide apparatus and methods for quantitating the relative volumes of the constituent phases of a fluid suspension without requiring the physical separation of the phases.

It is a further object of the present invention to provide apparatus and methods for fluorescent immunoassay that do not require the separation of a suspended phase from the sample before measurement.

Also, it is an object of the invention to provide for immunoassay of whole blood, saliva, and the like, with a single apparatus that compensates the measurements for the relative volume of the relevant portion (e.g., serum, etc.) of the sample.

BRIEF DESCRIPTION OF THE INVENTION

These and other objects are accomplished in the present invention of an assay apparatus and method employing total internal fluoresecence to define a thin observed volume of a multi-phase suspension from which the suspended phase, because of its size and shape, is substantially excluded. Observations of the fluorescence of a known quantity of fluorescent material introduced into a known volume of the sample containing the observed volume permits quantitation of the volumes of the suspended and suspending phases.

In a preferred embodiment, for use in immunoassay, a disposable consisting of a length of precise diameter capillary tubing having an approximately axially disposed optical fiber to which is immobilized a monolayer of a component of the antibody-antigen complex (e.g., an antibody) is employed. The disposable is also provided with an inert diluent, a preload of a known amount of tagged complement to the immobilized component (e.g., a fluorescent-tagged antigen), and a preload of a known amount of a second fluorescent material that, for example, fluoresces at a different wavelength than does the tag. The second fluorescent material is chosen and loaded so as to be non-reactive with the constituents of the sample but completely soluble in the anticipated volume of the relevant portion of the sample (e.g., the serum portion of whole blood or the liquid portion of saliva). The second fluorescent material is also chosen to have a diffusion rate at least as great as that of the tagged constituent and its complement.

In a preferred mode of operation, the fiber is immersed in a sample of interest, and allowed to remain for a sufficient time period for both the second fluorescent material and the tagged constituent and its complement to diffuse throughout the volume between the fiber and the capillary tube wall. The total sample volume through which the fluorescent material may diffuse is defined, inter alia, by the geometry of the fiber and the capillary tube. As the quantity of the second fluorescent material is preestablished, the concentration of the second fluorescent material in the suspending fluid portion of the sample is a measure of the fluid volume, being inversely proportional to the volume.

Observations of both fluorescent materials are made by total reflection fluorescence, an end of the fiber being both illuminated and observed within the fiber's numerical aperture. Only that portion of the fluorescent material within the evanescent wave fluoresces, and of this, only that which tunnels back into the fiber is observed. As a result, all that is observed of either the fluorescent tag (both immobilized to the fiber and suspended in the fluid) or the second, graduating, fluorescent material (now completely disolved in the suspending fluid) is within a few hundred Angstroms of the fiber. In part, the restriction of the fluorescent observations to a thin zone adjacent the fiber insures that the observation is primarily of the fluid constituent of the sample, the volume of the suspended phase (e.g., blood cells or bubbles) near the fiber being partially limited by the geometry of the suspended phase.

By appropriate optical filtering, the fluorescent signals due to the tag and to the disolved fluorescent material are individually processed, the signal due to the tag providing a titer of the immunologically reactive species within the total volume sampled, the signal due to the second fluorescent material providing a first-order measure of the concentration of the material, and hence the total volume of suspending fluid. A guard channel, observing the sample by attenuated total reflection at the fluorescence excitation wavelength, may also be used to provide a measure of any attenuation due to absorbing particles suspended in the fluid adjacent the fiber, thereby permitting a secondorder correction to the determination of the concentration of the sample.

Since the assay kit of the present invention contains the necessary reagents in the required quantity and dilution, and since its construction controls the total volume sampled and compensates for the suspended matter, little training or skill is required of the technician performing the assay, nor is any separation, precision volumetric, differential sensing, or timing apparatus required.

Inasmuch as fibers and capillary tubing of precise diameter and bore are readily and inexpensively available, and since the coating and loading of the fiber may be easily controlled during manufacture, it will be appreciated that the disposable of the present invention may be fabricated reasonably inexpensively.

Other objects of the invention will in part be obvious and will in part appear hereinafter. The invention accordingly comprises the apparatus possessing the construction, combination of elements, and arrangement of parts and the method comprising the several steps and the relation of one or more of such steps with respect to each of the others which are exemplified in the following detailed disclosure and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

In the figures, like index numbers refer to like elements.

With reference to terminology, it will be noted in the detailed description of the apparatus of this invention that portions of the apparatus are referred to as "upper" and "lower" portions. This is done wholly for convenience and to relate the description to the diagramatic representations in the drawings. It will be appreciated that the apparatus can function in any position or orientation and it is within the scope of this invention to have it do so.

It is further to be understood that the representation in the figures is diagramatic and no attempt has been made to indicate actual scales or ratios.

DETAILED DESCRIPTION

The present invention operates by total reflection fluorescence, coupled with tunneling of the fluorescent radiation, as described in Applicants' copending application Ser. No. 406,324, filed Aug. 9, 1982, to which reference may be had for further details of the optical mode of operation of the apparatus.

Although, as will be described, the invention may be practiced independently of other assays, thereby merely quantitating the relative volume of a constituent phase of a fluid suspension, it may be incorporated with advantage into certain other assays. In the latter cases, such combined apparatus and methods result not only in the obvious advantages of the combination (i.e., the quantitation of several items with but a single apparatus and procedure), but may also be used to simplify the protocol ordinarily required for the other assay. Immunoassays of biological fluids are such a case, since such fluids are generally suspensions, and since most protocols require separating the various constituent phases of the suspension as a preliminary to the immunoassay. For this reason, a preferred embodiment of the present invention is in conjunction with immunoassay, and it is with regard to such an embodiment that the invention will now be described. The disposable employed herein is similar to that described in copending application Ser. No. 410,340, filed Aug. 23, 1982, assigned to the assignee of the present application, and to which reference may be had for further details of its basic structure and operation.

Figure 1:
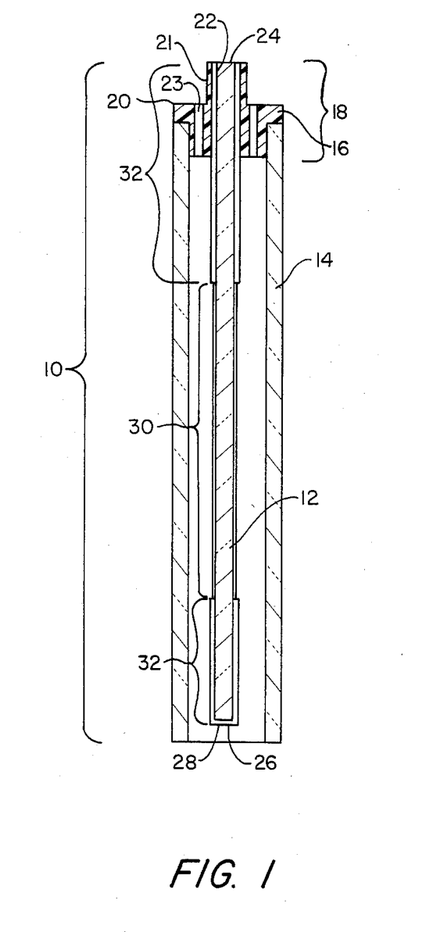
FIG. 1 is a longitudinal cross-sectional view of a disposable immunoassay kit which forms a preferred embodiment of the apparatus of the present invention.

Referring to FIG. 1, there may be seen a longitudinal cross-sectional view of an immunoassay kit 10 made in accordance with the principles of the present invention.

Kit 10 comprises optical fiber 12, capillary tube 14, and stopper 16.

Fiber 12 is an elongate substantially cylindrical optically transparent body adapted to propagate along its length through multiple total internal reflections optical radiation entering an end of the fiber within an established solid angle substantially rotationally symmetric about the fiber's axis. As is well known in the art of fiber optics, the maximum acceptance angle, with regard to the fiber axis, B, for the radiation entering the fiber and so propagated within it, is established by the refractive indices of the fiber and the surrounding medium. For radiation initially propagating through a medium of refractive index $n_0$, incident upon a fiber of refractive index $n_1$ otherwise surrounded by a material of refractive index $n_2$, the maximum acceptance angle may be found from the equation $$N.A. = n_0 \sin B = (n_1^2 - n_2^2)^{\frac{1}{2}} \qquad (1)$$

where N.A. is the so-called numerical aperture of the fiber. By way of example, but not limitation, fiber 12 may be any of a number of optically transparent materials, such as glass, quartz, polypropylene, polyamin, nylon, or the like, chosen to have an index of refraction greater than that of the fluid sample being assayed (typically, an aqueous solution having an index of refraction near 1.33 or a serum sample having an index of refraction near 1.35) and further chosen to be relatively insoluble and non-reactive with the fluid. While other fiber diameters may be used, it has been found that 200 microns is satisfactory. For most assays, a fiber 25 mm in length appears adequate; however, it will be understood that the length of the fiber can be accommodated to the assay to be undertaken.

Capillary tube 14 is preferably an optically transparent tube, its material of construction also being chosen to be relatively insoluble and nonreactive with the fluid being assayed. Thus, capillary tube 14 is preferably fabricated from such materials as glass, quartz, polypropylene, polyolefin, or the like. In a preferred embodiment, capillary tube 14 is of right circular cylindrical bore, having an inside diameter a few hundred microns larger than the diameter of fiber 12 (e.g., for a fiber diameter of 200 microns, capillary tube 14 may have an inside diameter of about 800 microns).

Stopper 16 is configured and dimensioned to fit within an end of capillary tube 14 and support an end portion 18 of fiber 12 substantially coaxially within the capillary tube. Additionally, stopper 16 provides a hard locating surface for positioning kit 10 in a fluorimeter, as will be described hereinafter. To these ends, stopper 16 is preferably provided with a flange 20 having an overall diameter on the order of the outside diameter of capillary tube 14 and a centrally disposed ferrule-like extension 21 coaxial with a central bore 22. Bore 22 penetrates throughout stopper 16, and is dimensioned to secure end portion 18 of fiber 12. In a preferred embodiment, stopper 16 is molded in place about fiber 12, the stopper being preferably fabricated of a low index material, such as siloxane. Stopper 16 is further provided with one or more through perforations 23 communicating with the interior of capillary tube 14.

Fiber 12 passes through and is supported by stopper 16 so as to expose substantially all of the fiber but end portion 18 to the interior of capillary tube 14, leaving end face 24 of end portion 18 unobscured and conterminous with the extremity of bore 22 external to the capillary tube. End face 24 is preferably planar and disposed normal to the axis of fiber 12. Preferably, end face 24 is also highly transparent and free of blemishes which would tend to scatter light incident upon the end face. To this end, end face 24 may be optically polished, although it has been found that a fused quartz fiber may be cleaved to provide an adequate optical surface. The end face 26 of the fiber distal from end face 24 is also polished flat or cleaved and further provided with a mirror coating 28 disposed substantially normal to the fiber axis, thereby causing radiation trapped in the fiber to double-pass the fiber. The overall dimensions of fiber 12, capillary tube 14, and stopper 16 are chosen to insure lower end face 26 of the fiber is within the capillary tube.

It will be understood that mirror coating 28 need not be provided, if but a single pass of the radiation is acceptable. In such an embodiment, however, it is necessary that end face 26 be made opaque, positioned outside capillary tube 14, or otherwise arranged to be clear of the fluid sample during measurements, in order to confine the volume sampled to the region defined by the evanescent wave, as will become apparent from the discussion infra of the operation of the device.

Prior to being assembled into kit 10, fiber 12 is provided a coating, as will be described, activating a region 30 of its cylindrical surface for the assay to be performed. In a preferred embodiment, the activated region 30 is restricted to a predetermined length of fiber 12 by a chemically and optically inert coating 32 of, for instance, low optical index silicone, extending over both ends of the fiber. It will be understood, however, that the dimensions of activated region 30 may be controlled by other means (e.g., by masking the fiber during coating), or, alternatively, the entire length of fiber 12 might be activated and the length of the fiber disposed within capillary tube 14 carefully controlled.

Figure 3:
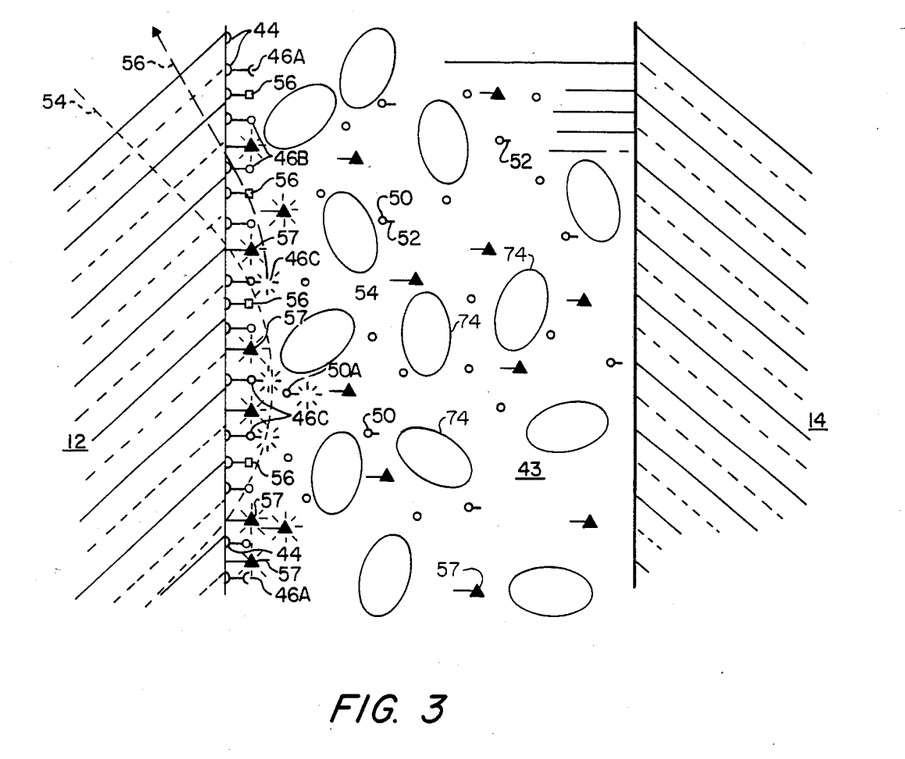
FIG. 3 is a stylized view of a portion of the kit of FIG. 1 (or 2), illustrating a typical immunochemical reaction in the realization of the invention.

Turning now to FIG. 3, there may be seen a highly stylized representation of a longitudinal cross-sectional portion of kit 10 within activated region 30 of fiber 12, filled with a sample 43 to be assayed.

The surface of fiber 12 within region 30 is provided with a plurality of coupling sites 44, to a number of which are bound a moiety 46 of the antibody-antigen complex of interest. (As used herein, the phrase "moiety of an antibody-antigen complex" refers to an immunologically reactive portion of such a complex, and includes haptens as well as complete antigens and antigen reactive antibody fragments [Fab] as well as complete antibodies). Coupling sites 44 are so selected as to immobilize moieties 46 without appreciably affecting the reactivity (e.g., the affinity and avidity) of the moiety for the complementary portion of the complex. In a preferred embodiment, fiber 12 is of glass or quartz, coupling sites 44 are the reactive groups of a silyl compound such as 3-aminopropyltrimethoxysilane, and moieties 46 are an antibody such as immunoglobulin G (IgG). As noted hereinabove, for this particular combination of solid phase, coupling site 44 and moiety 46 may be bound through the antibody's carboxyl terminations, thereby leaving the antibody's antigen reactive amino terminations free. The method for preparing the glass surface of fiber 12, of attaching the silyl compound thereto, and of covalently bonding an antibody to the glass through the silyl coupling, are described by Weetall (U.S. Pat. No. 3,652,761), where may also be found a description of other silyl compounds and the methods by which carboxyl, amino, and other reactive groups of antibody or antigen (or their fragments) may be covalently bound to various inorganic materials. It should be noted that an extensive art for immobilizing antigens or antibodies to polymers also exists, and those skilled in the art will understand that coupling sites 44 for antigen or antibody might be provided on polymeric fibers also. Thus, for instance, if fiber 12 is of nylon (polyamide), the coupling may be in the form of the substitution of an appropriate radical for the hydrogen bound to the polymer's functional groups.

It should be noted that coupling sites 44 may also incorporate spacer groups, as are well known in the art, to insure sufficient separation between fiber 12 and moieties 46 as to minimize steric hindrance of the antibody-antigen binding process. For example, coupling sites 44 might include a polyethylene chain, as for example in the case of 1,6 diaminohexane or 6 aminohexanoic acid bound to fiber 12 through a peptide bond and respectively providing a free primary amino and a free carboxyl group for covalently binding to the carboxyl or amino termination of a protein moiety 46. Either of these coupling materials provide a 6-carbon chain between terminations, thereby spacing moiety 46 from fiber 12 by the corresponding distance. Similar appropriate coupling and spacer materials are well known in the arts of both immunoassay and affinity chromatography.

In a preferred embodiment, fiber 12 is provided with moiety 46 having occupied binding sites, as indicated at index numerals 46C, the moieties being in part provided with attached tagged complement 50 for competition immunoassays. Thus, in one embodiment moiety 46 is an antibody, and a preloading of tagged antigen or hapten is incorporated into the coating of fiber 12. Each of the tagged components 50 is provided with a predetermined quantity of fluorophore 52, thereby providing a tag. The particular fluorescing compounds of interest for tagging include fluoresceine, tetramethylrhodamine, rare earth chelates, and the like. Methods for linking fluorescent tags to proteins are well known in the art, and many of the commercially available fluorescing compounds have groups for linking to proteins. Preferably, for competition assay, a fixed portion of coupling sites 44 are provided with a immunologically inert protein 56, such as albumin.

The active region of fiber 12 is also coated with a fixed quantity of immunologically inert fluorescent material 57. Fluorescent material 57 is chosen to be non-reactive with the sample or reagent and yet to be soluble in the suspending phase of the sample. Thus, for assays involving whole blood, fluorescent material 57 is chosen to be non-reactive with protein and to be soluble in blood serum. Further, fluorescent material 57 is chosen so as to fluoresce at a different wavelength than does the fluorescent tag attached to tagged complement 50. Then, too, fluorescent material 57 is chosen so as not to quench, or be quenched by, the fluorescent tag. Thus, to avoid radiation quenching, each of the fluorescent materials employed in a single assay is selected on the basis of not having an absorption maximum near the emmission maximum of the other fluorescent material (i.e., fluorescent material 57 and the tag of tagged complement 50 are each chosen on the basis of not having excitation band that overlaps the fluorescent emission band of the other).

Materials which may be used for fluorescent material 57 include such materials as Rhodamine B (C.I. No. 45170), Acridine Orange (C.I. No. 46005), berberine sulfate (C.I. No. 75,160), methylene blue (C.I. No. 52,015), thionine (C.I. No. 52000), pyrene, Astrazone orange R, various cyanines (such as 3,3' diethyloxadicarbocyanine iodide), quinacrine, ethidium bromide, and many others. Fluorescent material 57 is preloaded in sufficient quantity to be easily observable, but not sufficient to cause self-absorption. In these circumstances, fluorescent material 57 will be completely soluble in the anticipated volume of the suspending fluid component of the sample. As a guide, and subject to change depending upon the material and the sample, as will be understood by those skilled in the art of fluorescent assay, fluorescent material 57 typically may be preloaded to make up an approximately $10^{-9}$ to $10^{-6}$ molar solution in a volume of pure fluid that would occupy the space between active region 30 of fiber 12 and the adjacent wall of capillary tube 14. Fluorescent material 57 is weakly attached to fiber 12, as by hydrogen bonding.

The coating can be made to have a fixed surface composition by using adsorption phenomena, as follows. For a coating solution prepared with appropriate concentration of the reagents, mere immersion of a fiber activated with the proper surface binding groups 44 will produce a surface monolayer of chemically bound protein. The proportion of, say, immunoglobulin to inert protein in this layer will be given by (but not identical to) their proportion in the solution. Any partial filling of the immunoglobulin active sites with tagged antigen will of course be maintained at the level in the solution.

After dipping, the fiber is removed from the coating solution. To prevent the adhering liquid layer from entraining additional reagent, the fiber is then quickly washed before evaporation can occur. The protein layer, being covalently bound, will not be dislodged by this process. In order to prevent binding of more than one layer of protein, the bifunctional reagent must not alter the net charge of the protein (this can be controlled by adjusting the pH of the coating solution) and not have too long a spacer arm.

Figure 4:
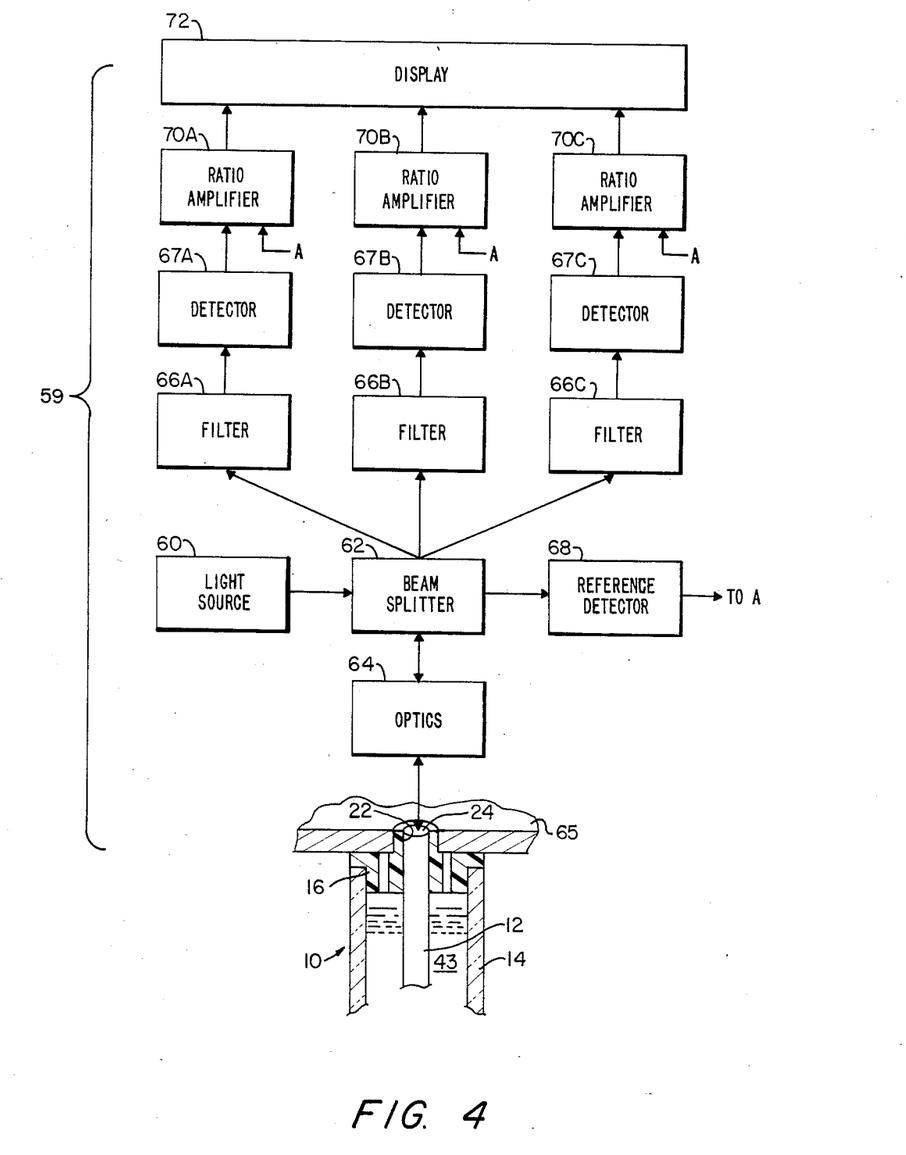
FIG. 4 is a partial schematic view and block diagram of an exemplary fluorometer for use with the immunoassay kit of the present invention.

Kit 10 is intended for use with fluorometer 59 (FIG. 4). Fluorometer 59 comprises light source 60, beam splitter 62, imaging optics 64, filters 66A, 66B, and 66C, detectors 67A, 67B, and 67C, reference detector 68, ratio amplifiers 70A, 70B, and 70C, and display 72.

Light source 60 provides optical radiation of the appropriate frequency, chosen on the basis of the fluorophore used as the tag and fluorescent material 57, so as to excite fluoresence in both components of the reagent. Light source 60 preferably provides this radiation over only a narrow wavelength band, chosen to maximize the fluorescence. Hence, light source 60 typically includes, in addition to the preferred tungsten-halogen lamp and associated power supply, a band-pass filter. Alternatively, it will be understood light source 60 might incorporate other sources, such as a mercury lamp, flash lamp, or a laser. Light source 60 also includes an appropriate beam shaping aperture and optics, as will be understood by those skilled in the art, to illuminate optics 64 with a beam of the appropriate vergence so as to permit the optics to image the source aperture on end face 24 of fiber 12 with no ray incident on the end face at an angle of incidence greater than that corresponding to the numerical aperture of the fiber.

Interposed between light source 60 and optics 64 is beam splitter 62. Beam splitter 62 is any of a number of well-known optical systems that can variously reflect and transmit a plurality of similar beams of radiation from one location to a plurality of other locations. Thus, beam splitter 62 incoporates partially reflecting mirrors or similar components, and is designed to project high frequency (short wavelength) fluorescence exciting radiation from light source 60 toward optics 64 and from optics 64 toward filter 66C while projecting low frequency (long wavelength) radiation from optics 64 toward filters 66A and 66B. Beam splitter 62 is further configured, by means well known in the art, to project radiation of a selected frequency from light source 60 toward reference detector 68.

Optics 64 are selected to image light source 60 on end face 24 of fiber 12, so as to just fill the end face with an image of the beam shaping aperture of the source, the maximum angle of incidence of a ray being selected to be no greater than that corresponding to the numerical aperture of the fiber. Optics 64 are also selected so as to collect substantially all of the radiation exiting end face 24 over the numerical aperture of the fiber and image the end face at photodetectors 66A, 66B, and 66C. As an aid in establishing the proper position of fiber 12, fluorimeter 59 is preferably provided with a positioning means, such as aperture plate 65, dimensioned to accept ferrule-like extension 22 of stopper 16 and disposed to position end face 24 appropriately relative to optics 64.

Detectors 67A and 67B include photodetectors, each of which is positioned to receive, through beam splitter 62 and filters 66A and 66B respectively, an image of end face 24 of fiber 12 projected toward the detectors by optics 64. Filters 66A and 66B, situated between beam splitter 62 and the respective detectors 67A and 67B, are respectively chosen to limit the radiation incident on the corresponding photodetector to the emission maxima of the fluorescent tag on tagged complement 50 and fluorescent material 57, respectively blocking the fluorescence of the other material. Thus, for instance, if the tag is fluorescein and fluorescent material 57 is ethidium bromide, filter 66A is chosen to pass a band of radiation about a wavelength of 520 nm (corresponding to the fluorescence maximum of fluorescein), and to reject a band from about 580 to 700 nm (corresponding to the fluorescence maximum of ethidium bromide). For such a combination of fluorescent materials, a dichroic beam splitter reflecting the 520 nm radiation and transmitting the 580 to 700 nm band might be used. The pass-and rejection-bands of filter 66B are preferably selected to be the reverse of those of filter 66A. As a result, radiation from the fluorescent tag collected by optics 62 is incident on detector 67A and flourescence due to fluorecent material 57 is incident on detector 67B.

Detectors 67A and 67B each preferably include a photomultiplier (provided with appropriate power supply and field optics to restrict the detector's field of view to end face 24, as is well known in the art), chosen to have maximum sensitivity in the region of peak fluorescence of the tag and fluorescent material 57, respectively. Detectors 67A and 67B are further preferably provided with blocking filters corresponding to the band-pass filter provided light source 60.

Filter 66C and detector 67C are also disposed to be illuminated by radiation exiting end face 24 of fiber 12 and collected by optics 64 and passed by beam splitter 62. Filter 66C is selected to transmit to detector 67C only that radiation incident upon it which is within the pass band of the band-pass filter provided light source 60, and detector 67C is chosen to have maximum sensitivity to this radiation. Detector 67C is also provided with power supply as required and field limiting stops (not shown) to restrict its field of view to end face 24 of fiber 12.

Reference detector 68, preferably a photodiode, is disposed to intercept radiation from light source 60 passing through beam splitter 62. Reference detector 68 is chosen for peak sensitivity in the spectral region of light source 60 passed by beam splitter 62, and includes appropriate field stops and optics to limit its field of view to the source.

Ratio amplifiers 70A, 70B, and 70C are any of a number of well-known electronic means each providing an output signal proportional to the ratio of a pair of input signals, so connected to the outputs of reference detector 68 and respectively to detectors 67A, 67B, and 67C as to provide signals proportional to the ratios of the outputs of the respective detectors to the reference detector. For instance, each ratio amplifier may be a variable gain amplifier amplifying the output from an individual detector 66 and having a gain inversely proportional to the output from reference detector 68.

The output of ratio amplifiers 70A, 70B, and 70C are connected to and serve as the inputs for display 72. Display 72 is any of a number of devices that provides three visual signals proportional to each of three electrical inputs, and may be, for instance, a set of meters or digital displays, a multi-trace strip chart recorder, or the like.

Kit 10 is primarily intended for use with fluid suspensions, although it will be understood that it could also be used with samples in which the various phases have been separated. As used herein, the term "suspension" means a non-homogeneous physico-chemical system having two or more physically distinct and mechanically separable portions (the so-called "phases" of the system) that are intermixed but undissolved in one another. The various phases of the suspension may be of the same or of different states (i.e., gaseous, liquid, or solid), although, as will become apparent, the suspending phase (also known as the continuous or external phase or the dispersion medium) must be fluid at least during a part of the operation of the apparatus of the invention.

In operation, kit 10 is dipped into a sample to be assayed. Perforations 23 allow capillary tube 14 to fill itself by capillary action once its end is immersed in sample (for the proposed tube diameter, it will be advantageous to hold the fiber at a slant for filling).

A fixed volume of sample will thus be drawn into capillary tube 14 whenever it is dipped in the solution and allowed to fill completely. Actually, a full capillary tube is not really required, it being sufficient only to have the liquid cover the entire active region 30 of fiber 12. This state can be verified by observing, through the wall of capillary tube 14, the sample to cover the upper inactivating coating 32 on the fiber. Consequently, it is not necessary to precisely control the capillary's length or its complete filling.

Once fiber 12 is immersed in the sample, fluorescent material 57 begins to disolve into the suspending fluid phase of the sample, and, by diffusion, tends toward a uniform concentration throughout the volume of the suspending phase contained between active region 30 of fiber 12 and the adjacent wall of capillary tube 14. At the same time, tagged complement 50 and the immunological reacting species of interest within the sample are diffusing away from and toward the fiber. The rate at which a uniform concentration of fluorescent material 57 within the suspending phase is reached depends upon the size of the fluorescent material, the temperature, and the viscosity of the sample. For typical values of these parameters, a uniform concentration within several hundred microns of active region 30 may be acheived in incubation times on the order of 15 minutes. A similar period of time is required for equilibration between the immunological reactants immobilized to fiber 12. (FIG. 3 corresponds to the situation before equilibration has been achieved; the loading of fluorescent material 57 onto fiber 12 is preferably such that at equilibration with the median sample about half the fluorescent material is in solution).

The total volume of the sample in which fluorescent material 57 is uniformly disolved in the suspending phase within such an incubation time (and the volume of the suspending phase scavenged for the immunologically reactive species of interest) substantially corresponds to the volume contained between fiber 12 and capillary tube 14 over the length of active region 30. The large length-to-diameter ratio of the active region insures that, for incubation time reasonably in excess of the minimum required incubation time, the length of the sample volume throughout which fluorescent material 57 is dispersed remains very nearly the length of active region 30.

In the case of interest, this total sample volume is not the sample volume of interest, as inclusions 74 (FIG. 3) void of the immunologically interesting species are suspended in sample 43. The desired data base volume corresponds to the volume of the suspending fluid phase surrounding inclusions 74 of (one or more) suspended phases. In the case of whole blood, inclusions 74 are cells (primarily erythrocytes of biconcave disklike form approximately 7.5 microns in diameter) that may comprise 50% or more of the total sample volume, while the suspending fluid (in this case, serum) correspondingly comprises the remaining volume. Fluorescent material 57, chosen to be nonreactive and non soluble with inclusions 74 (or, in the case of cells, chosen at least not to react with or penetrate the cell membrane) is only dispersed with the suspending fluid phase. As a pre-determined quantity of fluorescent material 57 has been allowed to disperse uniformly throughout the suspending fluid phase contained within the volume substantially defined by active region 30 and the adjacent inner wall of capillary tube 14, the concentration of the fluorescent material is a measure of the volume of the suspending fluid phase.

It will thus be understood that the concentration of fluorescent material 57, and therefore (ignoring quenching) the available fluorescence per unit volume of the suspending fluid due to the material, varies inversely as the total volume of the suspending phase through which the fluorescent material has been dispersed, having a minimum, corresponding to no inclusions 74 of a suspended phase, established by the geometry of fiber 12 and capillary 14 and by the quantity of fluorescent material preloaded into disposable 10, and a maximum, established by these parameters and by the tightest packing that may be achieved for the particular inclusions of the suspended phase. At the concentrations recommended, self-quenching of fluorescent material 57 is negligible. Consequently, a fluorescence measurement of a known volume of the suspending fluid phase will provide a measure of the total volume of the suspending phase assayed.

After incubation, kit 10 is placed in fluorometer 59, stopper 16 cooperating with aperture plate 65 to position end face 24 of fiber 12 in the appropriate location relative to the fluorimeter's optical train. Radiation of a wavelength chosen to excite fluorescence in fluorophores 52 and fluorescent material 57 is supplied by light source 60, via beam splitter 62 and optics 64, so as to illuminate end face 24 of fiber 12 within the cone angle defined by the numerical aperture of the fiber. This radiation is consequently propagated within fiber 12 at or above the critical angle (as indicated by ray 54 in FIG. 3), and multiply totally internally reflecting along the length of the fiber. As a result, an evanescent wave is produced in sample 43 adjacent the fiber.

As in copending applications 406,324 and 410,340, cited herinbefore, competitive binding of tagged components 50 and untagged components 54 to moieties 46 attached to the fiber results in fluorescently tagged complexes 46C in proportion to the relative concentration of tagged to untagged components. Excited by the evanescent wave, the tagged complexes 46C immediately adjacent fiber 12 fluoresce. A portion of the fluorescent emission tunnels into the fiber, propagating within the fiber along paths exceeding the critical angle, as indicated, for instance, by ray 56 in FIG. 3. Much of this totally reflected fluorescence emission exits the fiber at end face 24, where it is collected by optics 64 and projected through beam splitter 62 and filter 66A toward detector 67A. Filter 66A allows only radiation corresponding to the wavelength band of maximum fluorescence of tagged complexes 46C to pass to detector 67A, which in turn provides an electrical signal proportional to the intensity of this fluorescence. Beam splitter 62 also allows some radiation from source 60 to illuminate reference detector 68, which provides an electrical signal proportional to the source intensity. These two electrical signals are ratioed by ratio amplifier 70A to provide an electrical output signal proportional to fluorescent intensity of the immobilized tagged material corrected for source intensity variations, which is displayed by display 72.

In a similar manner, the evanescent wave exites fluorescence of that protion of material 57 immediately adjacent fiber 12. That portion of this fluorescence which tunnels back into fiber 12 and exits end face 24 is incident, via optics 64, beam splitter 62, and filter 66B, on detector 67B. Ratio amplifier 70B, in ratioing the signal from detector 70B and reference detector 68, provides a signal proportional to the fluorescence due to that portion of fluorescent material 57 adjacent fiber 12 corrected for source intensity variations. This signal is also displayed by display 72.

The size of the observed fluorescent zone, established by the evanescent wave and fluorescence tunnelling, together with the dimensions of active region 30 of fiber 12, establishes, to a first approximation, a fixed volume of the suspending fluid phase, the thinness of the layer restricting the percentage of this volume that can be occupied by an inclusion of a fixed shape. As an example, consider a concentration of about 50% by volume of 7.5 micron spheres distributed in contact with the surface of fiber 12. For such a situation, each 220 cubic micron sphere is surrounded on the average by some 440 cubic microns of suspending fluid. This volume ratio is easily achieved by cubic, rather than hexagonal, packing, and it follows that, at the fiber surface there will be some 56 square microns of suspending fluid for each (infinitesimal) point of contact with a spherical inclusion. Within, say, 1000 Angstroms of the surface of the fiber, each spherical inclusion will have a volume of about 0.1 cubic micron, while there will be some 5.5 cubic microns of suspending fluid for each inclusion. In such a case, a negligible error would be incurred in the estimation of the total volume of the suspending fluid assayed through failing to consider the reduction in the observed fluorescence due to sampling the non-fluorescent inclusions in the presumed fixed volume of suspending fluid. Actually, observed fluorescence zones having half-thicknesses on the order of a few hundred Angstroms may be achieved. Therefore, in principle, greater volume measuring accuracy may be achieved; however, in practice the accuracy suggested by the above example will not be observed because of the plastic flow likely to occur with the inclusions of interest.

To correct for the absorption loss in the effective fluorescent excitation zone, the absorption of the sample adjacent fiber 12 is observed by attenuated total reflection. That portion of the intensity of the evanescent wave that is absorbed in sample 43 results in a like reduction of the intensity of the totally reflected rediation within the fiber. The radiation propagating within the fiber from end face 24 toward end face 26 is reflected by mirror coating 28, and (less reflection and absorption losses) returned to end face 26. Optics 64 images this radiation, via beam splitter 62 and filter 66C, onto detector 67C. Filter 66C restricts the spectral region observed by detector 67C to that of the band pass filter of light source 60. Detector 67C thus observes the radiation due to source 60 that is not lost in the double-pass through fiber 12 or elsewhere in the system. The electrical output of detector 67C is ratioed with the output of reference detector 68 by ratio amplifier 70C, resulting in an output, corrected for source variations, proportional to transmittance of the system. This signal is also displayed by display 72. The transmittance, calibrated for known system losses, is a measure of the absorption due to sample 43. While a percentage of these losses are due to absorption of exciting radiation by the fluorescing materials in the sample, for the concentrations of interest, such losses are small. Thus, highly absorbing inclusions 74, such as erythrocytes, within the evanescent wave may be readily observed and quantitated by attenuated total reflection.

It will be appreciated that the present invention is not limited to the apparatus so far described nor to the experimental protocols outlined hereinabove. Thus, while the sample within tube 14 will be retained by capillarity as soon as the tube is withdrawn from the sample, evaporation at the sample's free surface will eventually reduce the sample within the tube. Accordingly, it may be advantageous to seal the tube with a nonfluorescent mastic as soon as the sample is collected. Alternatively, the sample may be protected from rapid evaporation by putting a terminal constriction, as generally indicated by index numeral 90 of kit 110 (FIG. 2) in capillary tube 114. Constriction 90 is limited to the region opposite the lower inert region 32 of fiber 12, and is typically given a minimum inside diameter some 100 microns greater than the diameter of the fiber (i.e., for the 200 micron fiber of the preferred embodiment, the minimum inside diameter of constriction 60 is some 300 microns). In all other respects, kit 110 may be similar to kit 10.

It will also be recognized that a portion of the reagents, and in particular, fluorescent material 57 could be in the form of a powder packed inside the capillary (for such an embodiment, the structure of capillary tube 114 recommends itself). However, fluorescent material 57 might also be coated on the the fiber or the inside wall of capillary tube 14 as a reagent coating 130 (illustrated in FIG. 2).

It will also be appreciated that other reagents, such as buffers, anticoagulants, and the like, might be packed within capillary tube 14 or coated on the fiber or capillary tube.

Figure 2:
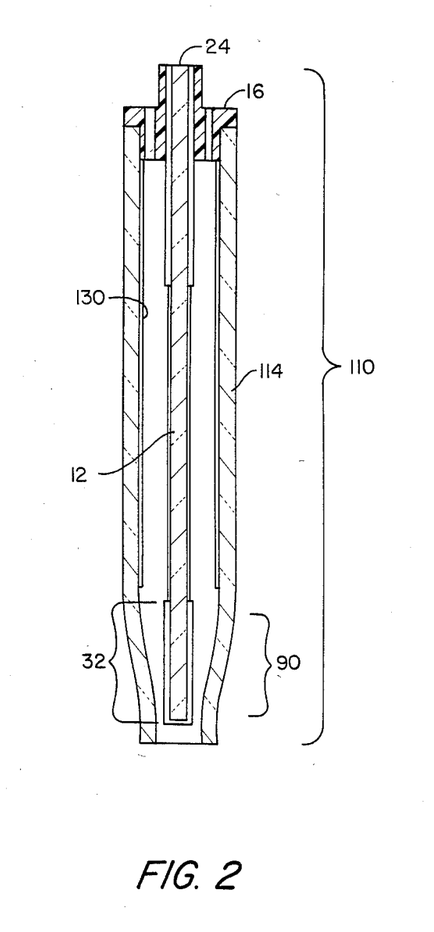
FIG. 2 is a view, similar to FIG. 1, of an alternative embodiment of the immunoassay kit of the present invention.

It might be noted further that the fiber diameter must not only be constant along its length, but must also be constant from disposable to disposable. Otherwise, while the overall amount of sample would be constant from test to test, the amount of reagent would vary. This accuracy requirement could be avoided by coating the tagged antigen on the inside wall of the capillary as reagent coating 130 (FIG. 2). This would not only reduce the diameter constancy requirement on the fiber but also on the capillary, since a diameter increase of the latter would increase not only the reagent amount but also that of the sample, while for the fiber, a resulting increase in the number of binding sites would be compensated by the reduction in the number of reflections (provided the illumination throughput was matched to the minimal fiber diameter).

It will also be understood that fiber 12 and tube 14 might be of other than right circular cylindrical shape, and that, for instance, they might be a pair of parallel plates with a capillary spacing therebetween.

Then again, it should be understood that the apparatus and methods of the present invention are not limited to immunoassay, but might be used for other assays in which a correction for the relative volumes of the phases of a suspension is necessary, or wherein additionally a measure of such a volume is desired. In fact, as previously noted, the methods and apparatus of the present invention are also intended for use with but a single reagent (soluble fluorescent material 57) merely to quantitate the relative volumes of the phases of a suspension. Thus, if the suspension is whole blood, a fluorescent material soluble in serum may be used to quantitate the cellular volume or hematocrit. For such applications, active region 30 of fiber 12 would not ordinarily be provided with immobilized moieties 46 of antigen or antibody, nor would kit 10 include tagged complement 50. It will also be understood that for merely quantitating the relative volumes of the phases of a suspension, a simplified fluorometer 59, not provided with a channel (filter 66A, detector 67A, and ratio amplifier 70A) corresponding to the region of peak fluorescence of the tag of tagged complement 50, might be used.

Since these and certain other changes may be made in the above apparatus and method without departing from the scope of the invention herein involved, it is intended that all matter contained in the above description or shown in the accompanying drawing shall be interpreted in an illustrative and not a limiting sense.

What is claimed is:

1. Apparatus for use in assays of fluid suspensions, said apparatus comprising:
means for delimiting a first volume of said fluid suspension;
means for introducing a pre-established quantity of a fluorescent material into said first volume, said fluorescent material being soluble in a unique fluid phase of said suspension and being capable when so dissolved of emitting fluorescent radiation when optically excited;
means for delimiting within said first volume a second volume limited to primarily a single phase of said suspension and throughout which fluorescence in said fluorescent material may be optically excited and observed.

2. Apparatus for use in immunoassays of a sample suspension containing an antigen-antibody complex incorporating a fluorescent tag capable of emitting fluorescent radiation over a first frequency band in response to a first predetermined band of exciting radiation, said apparatus comprising:
means for delimiting a first volume of said sample suspension;
means for introducing a pre-established quantity of a fluorescent material into said first volume, said fluorescent material being soluble in a unique fluid phase of said sample suspension and being capable when dissolved of emitting fluorescent radiation over a second frequency band when excited by a second predetermined band of said exciting radiation; and
means for delimiting within said first volume a second volume limited to primarily a single phase of said suspension and throughout which fluorescence in said first and second bands may be excited and observed.

3. Apparatus according to claim 2 wherein further said means for delimiting said first volume comprises (a) an optical element transmissive to radiation of said first and second predetermined bands of exciting radiation and to radiation of said first and second frequency bands, (b) an elongate enclosure means dimensioned to at least in part enclose said element in spaced-apart relationship of capillary dimensions, and (c) means for positioning said element in said relationship with said enclosure means.

4. Apparatus according to claim 3 wherein further said optical element is an optical fiber, said elongate enclosure means is a capillary tube, and wherein said means for providing a pre-established quantity of a fluorescent material is a soluble reagent coating on at least a portion of the interior wall of said capillary tube.

5. A method for assay of a fluid suspension, said method employing an optical element transmissive to excitation radiation which can excite fluorescence of a fluorescent material soluble in a unique fluid phase of said sample suspension, said optical element also being transmissive to fluorescence of said fluorescent material, said method comprising the steps of:
immersing a known area of said optical element in a fluid sample to be assayed;
controlling the immersion of said optical element so as to insure said known area is completely covered with a thin layer of said fluid sample of known thickness;
introducing a pre-established quantity of said fluorescent material into the volume of said fluid sample established by said known area and said known thickness;
incubating said optical element in said volume of fluid sample for a time in excess of the time required for diffusional processes to distribute said fluorescent material within said volume;
illuminating said optical element with radiation so as to excite fluorescence, by an evanescent wave, of said fluorescent material dissolved in said unique fluid phase; and
measuring the intensity of said fluorescence.

6. The method according to claim 5 and further including the steps of:

illuminating said optical element with radiation to which individual phases of said fluid suspension present substantially different individual transmissivities so as to form an evanescent wave of said radiation in said volume; and measuring, through attentuated total reflection, the absorption of said radiation by said sample suspension.

7. The method according to claim 6 wherein said absorption is of a frequency band corresponding to frequencies at which one of said individual phases of said fluid suspension is substantially transparent and includes frequencies at which the remaining phases of said fluid suspension are absorbing.

8. A method for immunoassay employing an optical element transmissive to excitation radiation which can excite fluorescence of a fluorescent tag included as a constituent of an antigen-antibody complex to be assayed in a sample suspension, said element being also transmissive to excitation radiation which can excite fluorescence of a second fluorescent material soluble in a unique fluid phase of said sample suspension, said element being also transmissive to fluorescence of said tag and of said second fluorescent material, said element having selected moieties of said antibody-antigen complex attached to a known area of its surface, said method comprising the steps of:

immersing said optical element in a sample suspension to be assayed so as to form said complex;

controlling the immersion of said optical element so as to insure said known area is completely covered with a thin layer of said sample of known thickness;

introducing a pre-established quantity of said second fluorescent material into the volume of said sample suspension established by said known area and said known thickness;

incubating said submerged optical element for a time in excess of the time required for diffusional processes to scavenge said volume;

illuminating said optical element with said excitation radiation so as to excite fluorescence, by an evanescent wave, of said tag in said complex attached to said element and said second fluorescent material dissolved in said unique fluid phase; and measuring the relative intensities of said fluorescence.

9. The method of immunoassay according to claim 8 and further including the steps of:

illuminating said optical element with radiation of a frequency band in which individual phases of said fluid suspension present appreciable absorption so as to form an evanescent wave of said radiation within said volume; and measuring, by attentuated total reflection, the absorption of said radiation by said sample suspension.

10. The method according to claim 9 wherein said frequency band corresponds to frequencies at which one of said individual phases of said fluid suspension is substantially transparent and includes frequencies at which the remaining phases of said fluid suspension are absorbing.

* * * * *